United States Patent [19]

Johnson

[11] 4,216,245

[45] Aug. 5, 1980

[54] METHOD OF MAKING PRINTED REAGENT TEST DEVICES

[75] Inventor: Leighton C. Johnson, Edwardsburg, Mich.

[73] Assignee: Miles Laboratories, Inc., Elkhart, Ind.

[21] Appl. No.: 927,892

[22] Filed: Jul. 25, 1978

Related U.S. Application Data

[60] Continuation-in-part of Ser. No. 779,824, Mar. 21, 1977, abandoned, which is a division of Ser. No. 701,403, Jun. 20, 1976, Pat. No. 4,046,513.

[51] Int. Cl.² ............................................. G01N 31/22
[52] U.S. Cl. ........................................ 427/2; 422/56; 422/57
[58] Field of Search ..................... 422/56, 57; 427/2

[56] References Cited

U.S. PATENT DOCUMENTS

| 3,127,281 | 3/1964 | Meyer | 422/57 |
| 3,549,328 | 11/1967 | Kilburn | 422/56 |
| 3,666,421 | 5/1972 | Price | 422/57 |
| 3,975,162 | 8/1976 | Renn | 422/56 |
| 3,996,006 | 12/1976 | Pagano | 422/56 |
| 4,087,332 | 5/1978 | Hansen | 195/127 |

*Primary Examiner*—Sam Silverberg
*Attorney, Agent, or Firm*—Edward H. Gorman, Jr.

[57] ABSTRACT

A test device for determining the presence of a constituent in a sample, and a method for making it are disclosed. The test device comprises reactants (e.g. reagents, enzymes, etc.) incorporated with a carrier matrix such that when the device is wetted with a test sample, the reactants and the constituent react to produce a detectable response. The reactants are positioned separately from each other on the matrix in substantially, discrete, non-contacting areas. Hence, reactants are maintained substantially separate from each other until the test device is wetted with the sample.

8 Claims, 5 Drawing Figures

METHOD OF MAKING PRINTED REAGENT TEST DEVICES

RELATED APPLICATION

This application is a continuation-in-part of U.S. application Ser. No. 779,824, filed Mar. 21, 1977, now abandoned which is, in turn, a divisional application of U.S. application Ser. No. 701,403, filed June 20, 1976 now U.S. Pat. No. 4,046,513.

BACKGROUND OF THE INVENTION

1. Field of the Invention

The present invention relates to a test device for determining the presence of a constituent in a sample. The invention as defined by the claims comprises a test device, and a method for preparing it, in which potentially incompatible reactants are kept separate from each other until the actual testing of a sample, such as a bodily fluid, takes place. Hence, the device comprises a carrier matrix incorporated with at least two reactants capable of interacting with a sample constituent being analyzed to produce a detectable response. The reactants are positioned separately from each other in substantially discrete, noncontacting areas on the carrier matrix.

2. Description of the Prior Art

The burgeoning field of test devices in the form of test strips has providing convenient and rapid analysis of various types of samples, including samples of biological, industrial, and automotive fluids, and the like. Diagnostic devices designed for detecting various clinically significant substances or constituents in biological fluids, such as urine and blood, including lysed or unlysed blood, blood plasma, and blood serum, have in many cases supplanted prior wet chemistry techniques which were both cumbersome and time-consuming. These diagnostic devices have thus assisted in the fast and accurate diagnosis and treatment of disease.

Conventional test strips generally comprise an absorbent or porous matrix incorporated with indicator reactants, usually of a colorimetric type. The sample to be tested is contacted with the matrix, such as by momentary immersion where the sample is liquid, and the indicator response is observed after a set period of time. For example, in a reagent strip for the detection of occult blood in urine a diagnostic strip can be employed which comprises an absorbent paper impregnated with o-tolidine and a peroxide. When this strip is wetted with urine containing occult blood, decomposition of the peroxide occurs with the accompanying oxidation of the o-tolidine to produce a color response. This test is sensitive and extremely useful in diagnosing urinary tract disorders. However, because of the relative incompatibility of employed reactants, shelf life has often been found to be relatively short and the strips can lose their sensitivity after long periods of storage.

Similar problems of reactant incompatibility occur in many other types of strips where more than one chemical reaction is involved. For example, reactants for testing ketone, blood urea nitrogen (BUN), and galactose levels have been known to have limited shelf lives. In order to explore ways of extending the shelf like of reagent test strips, i.e. methods of reducing the relative incompatibility of reactants, experiments were conducted to determine whether it would be possible to physically separate incompatible reagents on the strip itself. Prior to this work the successful separation of incompatible reagents had not been reported. The experiments were successful and it was found that reagent strips could indeed be prepared in which imcompatible reactants were physically separated until becoming contacted with the sample to be analyzed. Strips prepared in accordance with the present invention have excellent shelf life and are vastly superior in this respect to present commercial strips containing the same reactants.

SUMMARY OF THE INVENTION

The present invention relates to a test device for detecting a constituent in a sample, particularly a bodily fluid. The device comprises a carrier matrix incorporated with at least two different reactants capable of mutually interacting in the presence of the constituent to produce a detectable response, the different reactants being physically separated from each other on the matrix. The different reactants are printed separately on the matrix as a plurality of substantially discrete areas, including dots, microdots, lines or the like.

BRIEF DESCRIPTION OF THE DRAWINGS

Other and further advantages and features of the invention will be apparent to those skilled in the art from the following detailed description thereof, taken in conjunction with the accompanying drawings, in which:

FIGS. 1, 2 and 3 depict first and second reactant inks printed on a carrier matrix in first and second arrays of impressions, respectively. The impressions, or dots, of each array are shown interspersed, one with the other, in a substantially non-contacting spatial arrangement. FIG. 4 shows a 3-ink system printed in the same interspersed, substantially noncontacting arrangement. FIG. 5 portrays a case where the impressions which form first and second arrays of reactant inks are parallel lines.

DESCRIPTION OF THE PREFERRED EMBODIMENTS

In accordance with the present invention at least two reactant materials are arranged in separate arrays of impressions on a matrix. Circular dots represent an optimum shape for the impressions from the standpoint of packing density and reactant diffusions during an assay. The dots can be printed so as not to touch each other and dissimilar dots can be present in equal or unequal numbers as desired. Printed lines of varying widths and other impressions such as special symbols can be substituted for dots if desired. Moreover, an array can comprise impressions which differ in both shape and spatial arrangement. For example, impressions of one reactant ink can be spatially arranged more densely at one portion of the array than at another. Moreover the interspersion of non-contacting impressions of two inks need not be uniform or regular.

Figure 1:
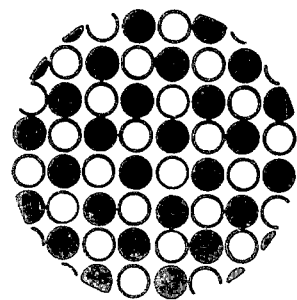
FIGS. 1 through 5 are diagrammatic illustrations of different patterns for applying reactants-containing inks in accordance with the present invention. All of the FIGS. depict cases where at least two inks are employed, FIG. 4 showing the use of three reactant inks. Thus.
Figure 2:
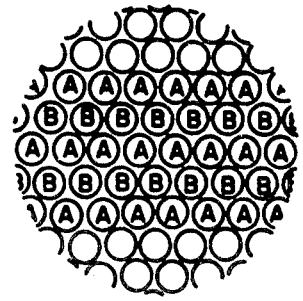
Figure 3:
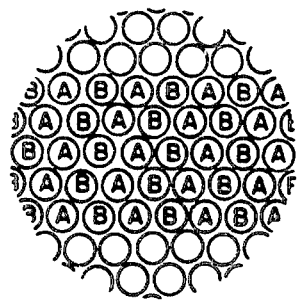
Figure 4:
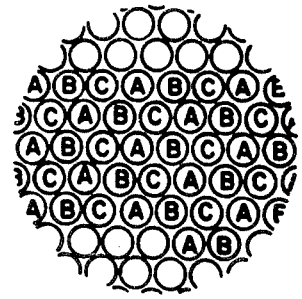

Referring to FIG. 1, one reactant is depicted as white dots, the second reactant being depicted as interspersed black dots. However, this arrangement is not the densest dot arrangement. Dots of the same reactant can be placed in a line (as A and B in FIG. 2) or can alternate on a line (as A and B in FIG. 3). FIG. 4 depicts a further pattern which is suitable where three different reactants (A, B and C) are employed. In FIG. 4 any reactant dot has six nearest neighbors which comprise three dots of each of the other two reactants.

Figure 5:
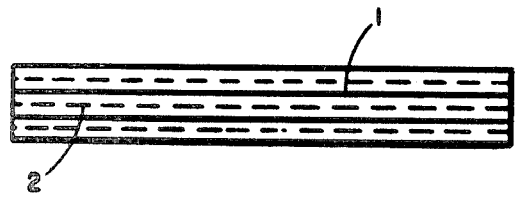

Another useful technique in separating the printed reactants is the application of recurring stripes to a carrier matrix. Hence, for a two reactant system, alternate stripes of the complimentary reactants can be laid out parallel on a matrix as in FIG. 5, in which solid recurring lines 1 represent a first reactant and dotted recurring lines 2 represent a second reactant.

The present invention has also been found to exhibit great utility in the deposition of enzymes entrapped in a polymer matrix. Hence, enzymes such as glucose oxidase can be printed in an ink containing acrylamide and a photopolymerization initiator such as potassium persulfate. Such an ink could be printed as dots, stripes, or other configurations and exposed after printing with a Number 2 photo flood lamp to effect polymerization.

In one embodiment of this particular entrapping technique, a stock solution of monomer compound is prepared by dissolving 40 g of acrylamide in 100 ml of 0.1 M phosphate buffer having a pH of 7.4. A cross linking reactant is prepared by dissolving 2.3 g of N,N-methylenebisacrylamide in 100 ml of 0.1 M phosphate buffer (pH 7.4). Gels can then be prepared by mixing these solutions in desired proportions together with a solution of an enzyme such as glucose oxidase. This gel can then be printed onto an inert matrix in accordance with the present invention and cured in situ.

Other applications of entrapped enzymes will be easily ascertainable by one skilled in the art by reference to U.S. Pat. Nos. 3,788,950, 3,793,445, 3,841,971, 3,859,169, and 3,935,071. These and other references in the prior art discuss in detail the physical entrapment of enzymes as well as enzymes covalently bound to a substrate and such techniques are readily applicable to the present invention.

In each of the above embodiments, whether dots or stripes, it can be seen that when the test device is wetted the separated reactants will at that time combine and interact with the constituent being analyzed. Typical test reactant compositions are set forth in U.S. Pat. Nos. 3,438,737; 3,095,277; 3,212,855; 3,164,534; 3,050,373; 2,981,606; 3,123,443; 3,252,762; 3,290,117; 3,092,463; 3,012,976; 3,122,420; 3,453,180; 3,585,001; 3,585,004; and 3,447,905 which are incorporated herein by reference.

The test device of the present invention is optimally prepared using printing techniques. For example, a polystyrene matrix can be printed with a first reactant ink and subsequently printed with a second reactant ink such that the first and second inks are imprinted in substantially non-contacting, coplanar impressions. Thus, in the case of an occult blood test device, a first ink containing o-tolidine is silk screened as a plurality of dots onto a polystyrene matrix. Subsequently, a second plurality of dots, juxtaposed with the first, is silk screened onto the matrix. The second plurality comprises a reagent ink containing a peroxide such as cumene hydroperoxide.

In another embodiment of the present invention, offset printing techniques are employed. An example of how this technique is employed in the present invention is the use of a rubber stamp containing raised dots. The rubber stamp is inked with a first reactant ink and applied to the matrix leaving a dot impression of the first reactant. The second reactant is stamped similarly onto the matrix except that the dots are juxtaposed with those of the first reactants.

Still another technique of preparing the present test device is that of applying ribbons or stripes of reactants separately onto the matrix. Thus each reactant ink is laid down alternately as parallel thin bands or concentric circles.

Normally, it is desirable to maintain the indicator composition, e.g. dye, for indicating a color change point as one of the separate discrete areas on the test device. For sample testing based on pH changes, it may also be desirable to maintain a buffer as a separate area on the test device until testing occurs.

It will be obvious to a person skilled in the art that many printing techniques can find applicability to the present invention. For example, it would be feasible to employ rotogravure printing techniques, silk screening, and offset printing. Of the foregoing methods, silk screening has to date been found to be preferred.

While silk is a preferred material for screening, screens made of other materials can also be employed, such as screens of woven polyester, polyamide or metal threads. Usually, art-known silk screens coated with standard photosensitive resist materials are employed. After photographic exposure of the screen (e.g. in the desired dot pattern) the exposed screen is washed, leaving the exposed pattern for printing. This technique, of course, is not novel and is too well known in the printing art to require further discussion herein. Preforated sheets made of a material such as plastic or thin metal can also be employed. A perforated sheet can be used in the same manner as a screen by placing the sheet over the inert matrix, applying reactant to it and drawing a doctor blade across it to spread the reactant material and force it through the holes thereby printing the matrix. The screens or sheets must be loaded precisely with respect to the inert matrix and the formulation of the reactants must be such that the desired result is achieved without the reactants running together during or after application. Regardless of the method employed, the size of the discrete reactant areas applied in known proportions can be varied from very small areas, e.g. microdot size, to relatively large size. The alignment of the printing apparatus obviously becomes more critical as the reactant areas become smaller and closer together.

The printing techniques described herein can be employed with any of conventional inert matrices used heretofore in diagnostic test devices, such as paper, plastic, and combinations thereof. The particular inert matrix chosen must be one which adequately reflects incident light since test devices are read by visually judging the intensity of reflected light from such devices. Optically transparent matrix materials such as Trycite ® polystyrene film made by Dow Chemical Co. may be employed.

If desired, paper used as a matrix can be coated to improve its light scattering efficiency and the printability of the paper, i.e. adherence of reactants. The surface of the paper can be white in color to reflect as much visible light of all wavelengths as possible. Obviously, a mat finish is preferred over a high gloss finish.

A plastic matrix can have essentially the same optical characteristics as noted for paper. While plastic has the advantage of being less chemically reactive and more uniformly reflective, adherence of reactants can be somewhat more difficult on plastic than paper using the printing techniques described herein. If desired a white pigment can be incorporated with the plastic to achieve a desired reflective surface.

Known diluent substances useful to reduce hygroscopicity of reactants, such as chloroform, carbon tetrachloride, benzene, and the like; as well as known wetting agents, such as diglycol laurate, organic phosphate esters of anionic detergents in ethanol and the like, which aid in producing an even diffusion of color on a test device can be incorporated into the printed reactant compositions of this invention.

Test devices in accordance with this invention can advantageously be made in the form of long strips or tapes that are rolled up and inserted in a suitable roll-tape dispenser as well as being cut into individual test strips.

The following examples are presented in order to more clearly describe the invention and to point out preferred embodiments. They are not, however, intended in any way to limit the present invention and are not to be thus interpreted.

EXAMPLE 1

ALTERNATE STRIPES

Two reactant inks were prepared as follows:
Polymer solution: A solution of cellulose acetate in acetone was prepared. This solution served separately as the vehiclw for each reactant.
Reactant 1:
In 65 ml of water was dissolved 2.8 g sodium citrate and 4.7 g citric acid. Next was added 50 mg of Tetrabromophenol Blue and 30 ml of methanol. The pH was then adjusted to 3.3 by the addition of a buffer. 10 ml of the resulting mixture was added to 20 ml of the polymer solution to produce a first reactant ink.
Reactant 2:
2.2 g of sodium citrate and 10 mg of orthocresol sulfonephthaline in 6 ml ethanol were added to 24 ml of water and the pH was adjusted to 7.8 through the addition of a buffer. 10 ml of this mixture was added to 20 ml of the polymer solution to form a second reactant ink.

A small dispensing head was prepared for applying the two inks to a polystyrene matrix. The dispensing head was provided with 14 channels approximately 0.03 inch in width. Two dispensing ports fed alternate sets of channels. Hence, the first port provided one ink sample to odd channels 1,3,5...13, the second provided the other ink sample to even channels 2,4,6...14. A portion of each ink was added to its respective port and the dispensing head was drawn across a white polystyrene matrix, thus depositing alternating stripes of the first and second inks. The striped polystyrene matrix was then cut into stripes about ¼ inch in width. These were tested with a 100 mg percent albumin solution in water and in pure water. The strip which was dipped in the albumin solution yielded a yellow/green color whereas an identical strip dipped in water became pale yellow.

EXAMPLE 2

Offset Dot Printing (Halftone)

This experiment was performed in order to demonstrate the feasibility of offset dot printing of reactants. A rubber plate for the printing was purchased from a local rubber stamping manufacturer. The manufacture of rubber plates is well known in the rubber stamp art, and the particular one purchased for this experiment was made using a metallic brass die containing normal printing periods as recessed dots. The periods were 30 mils in diameter and were squarely arranged in a density of 64 periods per square inch. An unvulcanized rubber matrix was placed over the die and pressure was applied causing the rubber to flow into the recesses of the metal die. Subsequently, heat was applied to the rubber to vulcanize it, causing the rubber plate to achieve a permanent configuration. The rubber sheet was then stripped off thus forming the rubber plate.

The rubber plate was cut into two squares, ½ inch on the side, thus forming the dies used for printing the reactant dots. Each rubber die was mounted using rubber cement to the face of an aluminum adapter used for mounting the die on a small arbor press which was commercially purchased.

Two reactant inks were prepared as in Example 1 for use with the dies. One of the dies was mounted on the press, and a piece of Trycite ® polystyrene film obtained from Dow Chemical Co. was mounted in the press beneath the die. The die was inked with the first reactant ink and an impression of the ink was made on the polystyrene film. The second die was then inked with the second reactant ink and mounted in the press. The register of the plastic film was changed such that the dots from the second die would be applied in a position juxtaposed with the first dots. The printing of the second dots completed the preparation of the test device, which was then air dried.

EXAMPLE 3

Silk Screen Dot Printing

This experiment demonstrates the application of the present invention to the silk screening printing process. A standard silk screen was purchased from Dec-O-Art, Inc. in Elkhart, Ind. This screen was photographically prepared by that corporation and contained patterns of 25 mil dots, 250 per square inch, and 40 mil dots, 125 per square inch. Thus, in the dot patterns on the silk screen, the dots constituted holes where an ink could flow through the screen, whereas all other areas in the dot pattern were closed to ink flow.

A sheet of Trycite ® polystyrene film obtained from Dow Chemical Co. was placed under the screen at a distance of from 1/16 to 3/16 inches. A portion of the first reactant ink from Example 1 was then drawn across the screen with the use of a square edged polyurethane squeegee. By exerting pressure on the squeegee, the screen contacted the polystyrene and a series of dots were laid down approximately the same size as the openings in the screen. The screen was then cleaned and a second series of dots was placed on the polystyrene using the second reactant ink of Example 1 except that the register of the screen was changed so that the second dots were juxtaposed with the first. The printed polystyrene sheet was then dried at ambient conditions, to form a usable printed test device.

The technique was repeated with the larger dots to likewise yield a satisfactory test device.

From the foregoing, it will be seen that this invention is well adapted to obtain all of the advantages hereinabove set forth, together with other advantages which are obvious and inherent to the system. The invention provides a rapid and relatively inexpensive method of applying reactants to a test device in a manner which prevents interaction of reactants until the test device is contacted with a sample to be tested. The shelf life of the test device is significantly improved.

Obviously, many other modifications and variations of the invention as hereinbefore set forth may be made without departing from the spirit and scope thereof.

What is claimed is:

1. In a method for preparing a dip-and-read test device for determining the presence of a constituent in a test sample, whereby said method comprises incorporating a carrier matrix with a reagent system comprising first and second reactants, said reactants mutually interacting in the presence of said constituent to produce a detectable response, the improvement which comprises
preparing a first reactant ink containing said first reactant, and a second reactant ink containing said second reactant,
printing said first ink onto said carrier matrix in a first array of impressions, and
printing said second ink onto said carrier matrix in a second array of impressions, the impressions of said second array being printed so as to be at least partially interspersed with, but substantially not contacting, the impressions of said first array.

2. The method of claim 1 in which the inks are printed by offset.

3. The method of claim 1 in which the inks are printed by screening.

4. The method of claim 1 in which the inks are printed by gravure.

5. The method of claim 1 in which the first ink is printed in a plurality of parallel stripes, and the second ink is likewise printed in stripes mutually parallel to and positioned between the first ink stripes.

6. In a method for preparing a dip-and-read test device for determining the presence of a constituent in a test sample, whereby said method comprises incorporating a carrier matrix with a reagent system comprising first and second reactants, said reactants mutually interacting in the presence of said constituent to produce a detectable response, the improvement which comprises
preparing a first reactant ink containing said first reactant, and a second reactant ink containing said second reactant,
silk screening said first ink onto said carrier matrix in a first array of impressions, and
silk screening said second ink onto said carrier matrix in a second array of impressions, the impressions of said second array being printed so as to be at least partially interspersed with, but substantially not contacting, the impressions of said first array.

7. The method of claim 6 in which the first and second patterns comprise dots.

8. The method of claim 6 in which the first and second patterns together comprise a plurality of parallel stripes, the stripes of the first reactant ink being alternately positioned with respect to the stripes of the second reactant ink.

* * * * *